US011555218B2

(12) United States Patent
Boutell (10) Patent No.: US 11,555,218 B2
(45) Date of Patent: Jan. 17, 2023

(54) SEQUENCING FROM MULTIPLE PRIMERS TO INCREASE DATA RATE AND DENSITY (71) Applicant: Illumina Cambridge Limited, Cambridge (GB)

(72) Inventor: Jonathan Mark Boutell, Bishops Stortford (GB)

(73) Assignee: Illumina Cambridge Limited, Cambridge (GB)

( * ) Notice: Subject to any disclaimer, the term of this patent is extended or adjusted under 35 U.S.C. 154(b) by 233 days.

(21) Appl. No.: 16/983,947

(22) Filed: Aug. 3, 2020

(65) Prior Publication Data
US 2020/0392573 A1 Dec. 17, 2020

Related U.S. Application Data (62) Division of application No. 15/510,191, filed as application No. PCT/GB2015/053324 on Nov. 4, 2015, now abandoned.

(30) Foreign Application Priority Data

Nov. 5, 2014 (GB) ..................... 1419731

(51) Int. Cl.
C12Q 1/6874 (2018.01)
G06T 7/00 (2017.01)

(52) U.S. Cl.
CPC .......... *C12Q 1/6874* (2013.01); *G06T 7/0012* (2013.01); *G06T 2207/30072* (2013.01)

(58) Field of Classification Search
CPC .............................................. C12Q 2535/122
See application file for complete search history.

(56) References Cited

U.S. PATENT DOCUMENTS

| | | | |
|---|---|---|---|
| 5,130,238 A | 7/1992 | Malek | |
| 5,185,243 A | 2/1993 | Ullman | |
| 5,455,166 A | 10/1995 | Walker | |
| 5,573,907 A | 11/1996 | Carrino | |
| 5,679,524 A | 10/1997 | Nikiforov | |
| 5,976,802 A | 11/1999 | Ansorge | |
| 6,172,218 B1 | 1/2001 | Brenner | |
| 6,210,891 B1 | 4/2001 | Nyren | |
| 6,214,587 B1 | 4/2001 | Dattagupta | |
| 6,258,568 B1 | 7/2001 | Nyren | |
| 6,274,320 B1 | 8/2001 | Rothberg | |
| 6,306,597 B1 | 10/2001 | Macevicz | |
| 6,969,488 B2 | 11/2005 | Bridgham | |
| 7,001,792 B2 | 2/2006 | Sauer | |
| 7,057,026 B2 | 6/2006 | Barnes | |
| 7,115,400 B1 | 10/2006 | Adessi | |
| 7,211,414 B2 | 5/2007 | Hardin | |
| 7,315,019 B2 | 1/2008 | Turner | |
| 7,329,492 B2 | 2/2008 | Hardin | |
| 7,405,281 B2 | 7/2008 | Xu | |
| 7,427,673 B2 | 9/2008 | Balasubramanian | |
| 7,582,420 B2 | 9/2009 | Oliphant | |
| 7,611,869 B2 | 11/2009 | Fan | |
| 7,670,810 B2 | 3/2010 | Gunderson | |
| 7,985,565 B2 | 7/2011 | Mayer | |
| 8,951,781 B2 | 2/2015 | Reed | |
| 2003/0219770 A1 | 11/2003 | Eshleman | |
| 2005/0100900 A1 | 5/2005 | Kawashima | |
| 2006/0188901 A1 | 8/2006 | Barnes | |
| 2006/0240439 A1 | 10/2006 | Smith | |
| 2006/0281109 A1 | 12/2006 | Ost | |
| 2007/0166705 A1 | 7/2007 | Milton | |
| 2008/0108082 A1 | 5/2008 | Rank | |
| 2009/0026082 A1 | 1/2009 | Rothberg | |
| 2009/0088327 A1 | 4/2009 | Rigatti | |
| 2009/0127589 A1 | 5/2009 | Rothberg | |
| 2009/0191565 A1 | 7/2009 | Lapidus | |
| 2009/0233802 A1* | 9/2009 | Bignell | ................ C12Q 1/6855 506/2 |
| 2009/0325172 A1 | 12/2009 | Milton | |
| 2010/0028885 A1 | 2/2010 | Balasubramanian | |
| 2010/0111768 A1 | 5/2010 | Banerjee | |
| 2010/0137143 A1 | 6/2010 | Rothberg | |
| 2010/0282617 A1 | 11/2010 | Rothberg | |
| 2012/0270305 A1 | 10/2012 | Reed | |
| 2013/0079232 A1 | 3/2013 | Kain | |
| 2013/0260372 A1 | 10/2013 | Buermann | |
| 2013/0274115 A1 | 10/2013 | Rigatti | |

FOREIGN PATENT DOCUMENTS

| | | |
|---|---|---|
| CN | 102140534 A | 8/2011 |
| CN | 103917654 A | 7/2014 |
| EP | 0 320 308 | 6/1989 |

(Continued)

OTHER PUBLICATIONS

Bentley, D.R., et al., Accurate whole human genome sequencing using reversible terminator chemistry, Nature, 456:53-59 (2008).
Bentley, D.R., et al., Accurate whole human genome sequencing using reversible terminator chemistry, Nature, 456:53-59 (2008), Supplementary Information (55 pages).
Cockroft, S. L., et al., A single-molecule nanopore device detects DNA polymerase activity with single-nucleotide resolution, J. Am. Chem. Soc. 130:818-820 (2008).
Deamer, D, et al, Characterization of nucleic acids by nanopore 25 analysis, Acc. Chem. Res. 35:817-825 (2002).

(Continued)

*Primary Examiner* — Teresa E Strzelecka (74) *Attorney, Agent, or Firm* — Knobbe Martens Olson & Bear (57) ABSTRACT

The present invention relates to a sequencing method which allows for increased rates of sequencing and an increase in the density of sequencing data. The system may be based on next generation sequencing methods such as sequencing by synthesis (SBS) but uses multiple primers bound at different positions on the same nucleic acid strand.

25 Claims, 4 Drawing Sheets

Specification includes a Sequence Listing.

(56) References Cited

FOREIGN PATENT DOCUMENTS

| EP | 0 336 731 | 10/1989 |
|---|---|---|
| EP | 0 439 182 | 7/1991 |
| WO | WO 1989/09835 | 10/1989 |
| WO | WO 1989/012696 | 12/1989 |
| WO | WO 1990/001069 | 2/1990 |
| WO | WO 1991/06678 | 5/1991 |
| WO | WO 2004/018497 | 3/2004 |
| WO | WO 2005/065814 | 7/2005 |
| WO | WO 2006/064199 | 6/2006 |
| WO | WO 2007/010251 | 1/2007 |
| WO | WO 2007/123744 | 11/2007 |

OTHER PUBLICATIONS

Deamer, D. W, et al, Nanopores and nucleic acids: prospects for ultrarapid sequencing, Trends Biotechnol. 18:147-151 (2000).
Dean et al., Comprehensive human genome amplification using multiple displacement amplification, Proc. Natl. Acad. Sci. USA 99:5261-66 (2002).
Grothues et al. PCR amplification of megabase DNA with tagged random primers (T-PCR), Nucleic Acids Res. 21(5):1321-2 (1993).
Healy, K., Nanopore-based single molecule DNA analysis, Nanomed. 2: 459-481 (2007).
Korlach, J. et al., Selective aluminum passivation for targeted immobilization of single DNA polymerase molecules in zero-mode waveguide nano structures, Proc. Natl. Acad. Sci. USA 105:1176-1181 (2008).
Lage et al., Whole Genome Analysis of Genetic Alterations in Small DNA Samples Using Hyperbranched Stand Displacement Amplification and Array—CGH, Genome Research 13:294-307 (2003).
Levene, M. J. et al., Zero-mode waveguides for single-molecule analysis at high concentrations, Science 299:682-686 (2003).
Li, J., M., et al, DNA molecules and configurations in a solid-state nanopore microscope, Nat. Mater. 2:611-615 (2003).
Lizardi et al., Mutation detection and single-molecule counting using isothermal rolling-circle amplification, Nat. Genet. 19:225-232 (1998).
Lundquist, P. M. et al., Parallel confocal detection of single molecules in real time, Opt. Lett. 33:1026-1028 (2008).
Metzker, Applications of Next-Generation Sequencing, Sequencing Technologies—the next generation, Nature Reviews Genetics, 11(1):31-46 (2010).
Metzker, Emerging technologies in DNA sequencing, Genome Res. 15:1767-1776 (2005).
Ronaghi, M., Pyrosequencing sheds light on DNA sequencing, Genome Res. 11(1):3-11 (2001).
Ronaghi, M., et al, Real-time DNA sequencing using detection of pyrophosphate release, Analytical 15 Biochemistry 242(1) 84-9 (1996).
Ronaghi, M, et al, A sequencing method based on real-time pyrophosphate, Science 281(5375):363 (1998).
Ruparel et al., Design and synthesis of a 3'-O-allyl photocleavable fluorescent nucleotide as a reversible terminator for DNA sequencing by synthesis, Proc Natl Acad Sci USA 102:5932-7 (2005).
Soni, G. V., et al. A. Progress toward ultrafast DNA sequencing using solidstate nanopores, Clin. Chem. 53:1996-2001 (2007).
Walker et al., Strand displacement amplification—an isothermal, in vitro DNA amplification technique, Nucl. Acids Res. 20:1691-96 (1992).
Wiemann, et al, Doublex Flourescent DNA Sequencing: Two Independent Sequences Obtained Simultaneously in One Reaction with Internal Labeling and Unlabeled Primers, Anal Bionchem, 234(2):166-174 (1996).

* cited by examiner

Bold = P5, underline = SBS3, italics = SBS8, italics & bold = P7

AATGATACGGCGACCACCGAGATCTACACTCTTTCCCTACCACGACGGCTCTTCCGATCT---insert---*AGATCGGAAGAGCGGTTCAGCAGGAATGCCGAGACCGATCTCGTATGCCGTCTTCTGCTTG*

TTACTATGCCGCGGCTGGTGGCTCTAGATGTGAGAAAGGGATGGTGCTGCCGAGAAGGCTAGA---insert---*TCTAGCCTTCTCGCCAAGTCGTCCTTACGGCTCGTGG*CTGGCTAGAGCATACGGCAGAAGACGAAC

←—— SBS3

←—— SBS8'

SEQUENCE LISTING

<160> NUMBER OF SEQ ID NOS: 6

<210> SEQ ID NO 1
<211> LENGTH: 120
<212> TYPE: DNA
<213> ORGANISM: Homo sapiens

<400> SEQUENCE: 1
aatgatacgg cgaccaccga gatctacact ctttccctac cacgacgctc ttccgatcta    60

-continued

```
gatcggaaga gcggttcagc aggaatgccg agaccgatct cgtatgccgt cttctgcttg    120

<210> SEQ ID NO 2
<211> LENGTH: 120
<212> TYPE: DNA
<213> ORGANISM: Homo sapiens

<400> SEQUENCE: 2
ttactatgcc gctggtggct ctagatgtga gaaagggatg gtgctgcgag aaggctagat     60
ctagccttct cgccaagtcg tccttacggc tctggctaga gcatacggca gaagacgaac    120

<210> SEQ ID NO 3
<211> LENGTH: 59
<212> TYPE: DNA
<213> ORGANISM: homo sapiens

<400> SEQUENCE: 3
aatgatacgg cgaccaccga gatctacact ctttccctac cacgacgctc ttccgatct      59

<210> SEQ ID NO 4
<211> LENGTH: 59
<212> TYPE: DNA
<213> ORGANISM: homo sapiens

<400> SEQUENCE: 4
ttactatgcc gctggtggct ctagatgtga gaaagggatg gtgctgcgag aaggctaga      59

<210> SEQ ID NO 5
<211> LENGTH: 61
<212> TYPE: DNA
<213> ORGANISM: homo sapiens

<400> SEQUENCE: 5
agatcggaag agcggttcag caggaatgcc gagaccgatc tcgtatgccg tcttctgctt     60
g                                                                    61

<210> SEQ ID NO 6
<211> LENGTH: 61
<212> TYPE: DNA
<213> ORGANISM: homo sapiens

<400> SEQUENCE: 6
tctagccttc tcgccaagtc gtccttacgg ctctggctag agcatacggc agaagacgaa     60
c                                                                    61
```

SEQUENCING FROM MULTIPLE PRIMERS TO INCREASE DATA RATE AND DENSITY

CROSS-REFERENCE TO RELATED APPLICATIONS

This application is a divisional of U.S. patent application Ser. No. 15/510,191 filed Mar. 9, 2017, which is the U.S. national phase of PCT Application No. PCT/GB2015/053324 filed Nov. 4, 2015 and published in English as WO 2016/071689 on May 12, 2016 and which claims the benefit of GB Application No. GB 1419731.3 filed Nov. 5, 2014, the contents of which are incorporated by reference in their entireties.

REFERENCE TO SEQUENCE LISTING

The present application is being filed along with a Sequence Listing in electronic format. The Sequence Listing is provided as a file entitled ILLINC366D1SEQLISTING, created Mar. 9, 2017, which is approximately 1.5 Kb in size. The information in the electronic format of the Sequence Listing is incorporated herein by reference in its entirety.

The present invention relates to a sequencing method which allows for increased rates of sequencing and an increase in the density of sequencing data. The system may be based on next generation sequencing methods such as sequencing by synthesis (SBS) but uses multiple primers bound at different positions on the same nucleic acid strand.

Deciphering DNA sequences is essential for virtually all branches of biological research. With the advent of Sanger sequencing, scientists gained the ability to elucidate genetic information from any given biological system. This technology has become widely adopted in laboratories around the world, yet has always been hampered by inherent limitations in throughput, scalability, speed, and resolution that often preclude scientists from obtaining the essential information they need. To overcome these barriers, Next-Generation Sequencing (NGS) was developed, a fundamentally different approach to sequencing that triggered numerous ground-breaking discoveries and ignited a revolution in genomic science.

Next-Generation Sequencing data output initially increased at a rate that outpaces Moore's law, more than doubling each year since it was invented. In 2007, a single sequencing run could produce a maximum of around one gigabase (Gb) of data. By 2011, that rate has nearly reached a terabase (Tb) of data in a single sequencing run—nearly a 1000× increase in four years. With the ability to rapidly generate large volumes of sequencing data, Next-Generation Sequencing enables researchers to move quickly from an idea to full data sets in a matter of hours or days. Researchers can now sequence 16 human genomes in a single run, producing data in roughly 3 days, for a reagent cost per genome that is still decreasing.

By comparison, the first human genome required roughly 10 years to sequence using CE technology and an additional three years to finish the analysis. The completed project was published in 2003, just a few years before Next-Generation Sequencing was invented, and came with a price tag nearing 3 billion USD.

While the latest high-throughput sequencing instruments are capable of massive data output, Next-Generation Sequencing technology is highly scalable. The same underlying chemistry can be used for lower output volumes for targeted studies or smaller genomes. This scalability gives researchers the flexibility to design studies that best suit the needs of their particular research. For sequencing small bacterial/viral genomes or targeted regions like exomes, a researcher can choose to use a lower output instrument and process a smaller number of samples per run, or can opt to process a large number of samples by multiplexing on a high-throughput instrument. Multiplexing enables large sample numbers to be simultaneously sequenced during a single experiment.

Although Next-Generation Sequencing has increased output significantly, there is still benefit in increasing the data rate and density of sequencing, particularly when working with large genomes for example. The present invention aims to further improve the data rate and the data density/yield, particularly when applied to Next-Generation Sequencing/sequencing by synthesis (SBS) methodology.

Preferably the term "base call", base calls or base calling refers to the process of assigning bases (nucleobases) to the information obtained during sequencing e.g. by assigning nucleotides to chromatogram peaks.

As used herein, and unless stated otherwise, each of the following terms shall have the definition set forth below.

A—Adenine;
C—Cytosine;
DNA—Deoxyribonucleic acid;
G—Guanine;
RNA—Ribonucleic acid;
T—Thymine; and
U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to A, G, C, T or U.

"Mass tag" shall mean a molecular entity of a predetermined size which is capable of being attached by a cleavable bond to another entity.

"Solid substrate" shall mean any suitable medium present in the solid phase to which an antibody or an agent may be affixed.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

One aspect of the invention provides a method for determining the sequence of a nucleic acid comprising providing at least one nucleic acid bound to a support;

hybridising at least two primers to the same strand of nucleic acid;

performing primer extensions on the said same strand of nucleic acid at each of the at least two primers;

obtaining signal data corresponding to at least one nucleotide base incorporated at each of the primer extensions;

determining from said signal data the identity of the nucleotide bases and allocating said bases to an extension read.

Preferably, the method comprises contacting the nucleic acid with an enzyme in the presence of (i) the at least two primers able to hybridise to the same strand of said nucleic acid at different positions and (ii) four labelled moieties comprising at least one nucleotide analogue selected from dGTP, dCTP, dTTP, dUTP, and dATP, each of the four labelled moieties having a unique label which is different from the unique labels of the other three labelled moieties, under conditions permitting hybridisation to give a plurality of extensions reads, each extension read extending from one of the at least two primers.

The method may comprise the step of removing unbound labelled moieties.

Preferably, the plurality of extension reads comprise substantially simultaneous extension reads.

In certain embodiments, the four labelled moieties each comprise a single reversibly terminating nucleotide analogue or reversible terminator analogue selected from dGTP, dCTP, dTTP, dUTP, and dATP or an oligonucleotide probe comprising at least one nucleotide analogue selected from dGTP, dCTP, dTTP, dUTP, and dATP.

Advantageously, the signal data corresponding to each of the at least two primer extensions may be obtained substantially simultaneously.

This provides the advantage that the signal data comprises data corresponding to multiple signals from the same nucleic acid strand.

Optionally, the signal data comprises one or more images.

Optionally, the signal data is detected as colour signals corresponding to a plurality of nucleotide analogues incorporated the primer extensions and wherein each colour signal corresponds to a different nucleotide analogue or combination of nucleotide analogues.

One aspect of the present invention provides a method for determining the sequence of a nucleic acid comprising performing the following steps:

(a) providing at least one nucleic acid bound to a support;

(b) contacting the nucleic acid with an enzyme in the presence of (i) at least two primers able to hybridise to the same strand of said nucleic acid at different positions and (ii) four probes comprising at least one nucleotide analogue selected from dGTP, dCTP, dTTP, dUTP, and dATP, each of the four probes having a unique label which is different from the unique labels of the other three probes, under conditions permitting hybridisation to give a plurality of extensions reads, each extension read extending from one of the at least two primers, (c) removing unbound probes;

(d) determining the identity of the nucleotide analogues incorporated in step (b) via determining the identity of the corresponding unique labels, and (e) allocating nucleotide bases to an extension read.

Preferably the plurality of extension reads comprise simultaneous extension reads.

In certain embodiments, the method comprises sequencing by synthesis and the enzyme comprises a polymerase.

The four probes may each comprise a single reversibly terminating nucleotide analogue or reversible terminator analogue selected from dGTP, dCTP, dTTP, dUTP, and dATP.

In certain embodiments, the method comprises sequencing by ligation and the enzyme comprises a ligase.

The four probes may comprise oligonucleotides.

The oligonucleotides may be of the type used in sequencing by ligation techniques.

The method may comprise sequencing by synthesis, sequencing by ligation, pyrosequencing or nanopore sequencing.

In certain embodiments, each unique label is detectable as a different colour.

Advantageously as two or more primers are hybridised to the same strand of nucleic acid but at different positions this allows sequencing of the strand to begin at two separate points, to give multiple extension reads, potentially multiplying the density of data and the rate at which it is obtained. When the system uses nucleic acids bound to a solid support, for example in next generation sequencing techniques, this allows for multiple base calls to be made at each particular location. Each base call is allocated to the correct extension read which allows the sequence of the nucleic acid to be determined.

In certain embodiments, the method provides the advantage that a plurality of nucleotide bases incorporated into a single template strand of a nucleic acid at different positions on the same strand may be identified simultaneously in real time.

Preferably the nucleic acid is deoxyribonucleic acid (DNA).

Preferably the nucleic acid is bound to a solid substrate.

Most preferably the solid substrate is of the type used in sequencing by synthesis or sequencing by ligation methodologies.

Preferably the solid substrate is a chip.

Alternatively the solid substrate is a bead.

Optionally the unique label is bound to a base via a cleavable linker

Optionally the unique label is bound to the base via a chemically cleavable or photocleavable linker.

Optionally the unique label is a dye, a fluorophore, a chromophore, a combinatorial fluorescence energy transfer tag, a mass tag, or an electrophore.

Preferably, after (a) providing at least one nucleic acid bound to a support; the nucleic acid is amplified.

Most preferably the nucleic acid is amplified by bridge amplification.

Optionally, the at least two primers able to hybridise to the same strand of said nucleic acid at different positions have overlapping sequences.

Optionally, a second primer is the same as a first primer with one additional base at the end. Additional primers could also be used each adding an additional base.

Optionally, blocked and unblocked primers are used to chemically differentiate between extension reads. This ensures that correct base calls are allocated to the correct extension read.

This may be achieved by using differing levels of blocked and unblocked primers for each of the at least two primers used.

Optionally, bioinformatics information is used to allocate said bases to an extension read.

In certain embodiments, the step of determining the identity of the nucleotide analogues comprises detecting signal data corresponding to the plurality of extension reads.

The signal data corresponding to each of the plurality of extension reads may be simultaneously detected.

The step of determining the identity of the nucleotide analogues may comprise analysing a signal intensity profile corresponding to the unique labels detected at each of the extension reads.

This may include measuring signal intensities in the signal data corresponding to each extension read simultaneously.

Optionally, the method includes determining the distribution of intensity measurements in the signal data by generating a histogram of intensity data.

The signal data may be detected as colour signals corresponding to a plurality of nucleotide analogues incorporated in step (b), wherein each colour signal corresponds to a different nucleotide analogue or combination of nucleotide analogues.

The method may include the step of signal processing comprising one or more of signal deconvolution, signal refinement and signal selection.

The method may include selecting colour signals of highest intensity at each extension read to provide a base call.

Multiple base calls may be made at each hybridisation cycle.

Optionally, the step of allocating bases to an extension read comprises determining the position of the nucleotide analogues.

Optionally, the step of allocating bases to an extension read comprises providing a preliminary base call and a final base call for each extension read.

Optionally, the final base call is provided by comparison of the preliminary base call data with a reference genome.

Optionally, the final base call is provided by comparison of the preliminary base call data with a reference genome.

In certain embodiments, the at least two primers may be overlapping primers.

In certain embodiments, the at least two primers may differ by a single base addition.

Advantageously, in certain embodiments, the method provides detecting a signal comprising signal data corresponding to a plurality of substantially simultaneous primer extensions at distinct sites on the same nucleic acid strand or molecule.

Advantageously, no more than four unique labels corresponding to single nucleotide monomer analogues of dGTP, dCTP, dTTP, dUTP, and dATP or to oligonucleotide probes comprising analogues of dGTP, dCTP, dTTP, dUTP, and dATP may be required in the method.

The same set of four probes are preferably used in the method for each extension read.

According to the present invention there is provided a method for determining the sequence of a nucleic acid comprising performing the following steps for each residue of the nucleic acid to be sequenced:

(a) providing at least one nucleic acid bound to a support;

(b) contacting the nucleic acid with a nucleic acid polymerase in the presence of (i) at least two primers able to hybridise to the same strand of said nucleic acid at different positions and (ii) four reversibly terminating nucleotide analogues or reversible terminators selected from analogues of dGTP, dCTP, dTTP, dUTP, and dATP, each of the four analogues having a unique label which is different than the unique labels of the other three analogues, under conditions permitting the polymerase to catalyze nucleic acid synthesis to give a plurality of extensions reads, each extension read extending from a primer, (c) removing unbound nucleotide analogues;

(d) determining the identity of the nucleotide analogues incorporated in step (b) via determining the identity of the corresponding unique labels, and (e) allocating said bases to an extension read.

Yet another aspect of the present invention provides a system for determining the sequence of a nucleic acid comprising sequencing apparatus having a solid support for immobilising at least one nucleic acid and means for determining its sequence by contacting the nucleic acid with an enzyme in the presence of (i) at least two primers able to hybridise to the same strand of said nucleic acid at different positions and (ii) four probes comprising at least one nucleotide analogue selected from dGTP, dCTP, dTTP, dUTP, and dATP, each of the four probes having a unique label which is different from the unique labels of the other three probes, under conditions permitting hybridisation to give a plurality of extensions reads, each extension read extending from one of the at least two primers;

removing unbound probes;

determining the identity of the nucleotide analogues incorporated via determining the identity of the corresponding unique labels, and allocating nucleotide bases to an extension read.

Another aspect of the present invention provides a method of sequencing comprising providing at least one nucleic acid hybridised to a support;

hybridising at least two primers to the same strand of nucleic acid to provide two extension reads;

performing an extension of each of the primers with reversible terminator bases;

obtaining an image of the bound reversible terminator bases for each base addition;

determining from said images the plurality of bases present at a location on the support and allocating said bases to an extension read.

Yet another aspect of the present invention provides a system for determining the sequence of a nucleic acid comprising sequencing apparatus having a solid support for immobilising at least one nucleic acid and means for providing at least one nucleic acid bound to a support;

hybridising at least two primers to the same strand of nucleic acid;

performing at least two primer extensions on the said same strand of nucleic acid at each of the at least two primers;

obtaining signal data corresponding to at least one nucleotide base incorporated at each of the at least two primer extensions;

determining from said signal data the identity of the nucleotide bases and allocating said bases to an extension read.

Preferably, the system comprises a signal processor for processing the signal data.

Yet another aspect of the present invention provides a kit for determining the sequence of a nucleic acid comprising sequencing reagents and instructions for performing the method.

Figure 1:
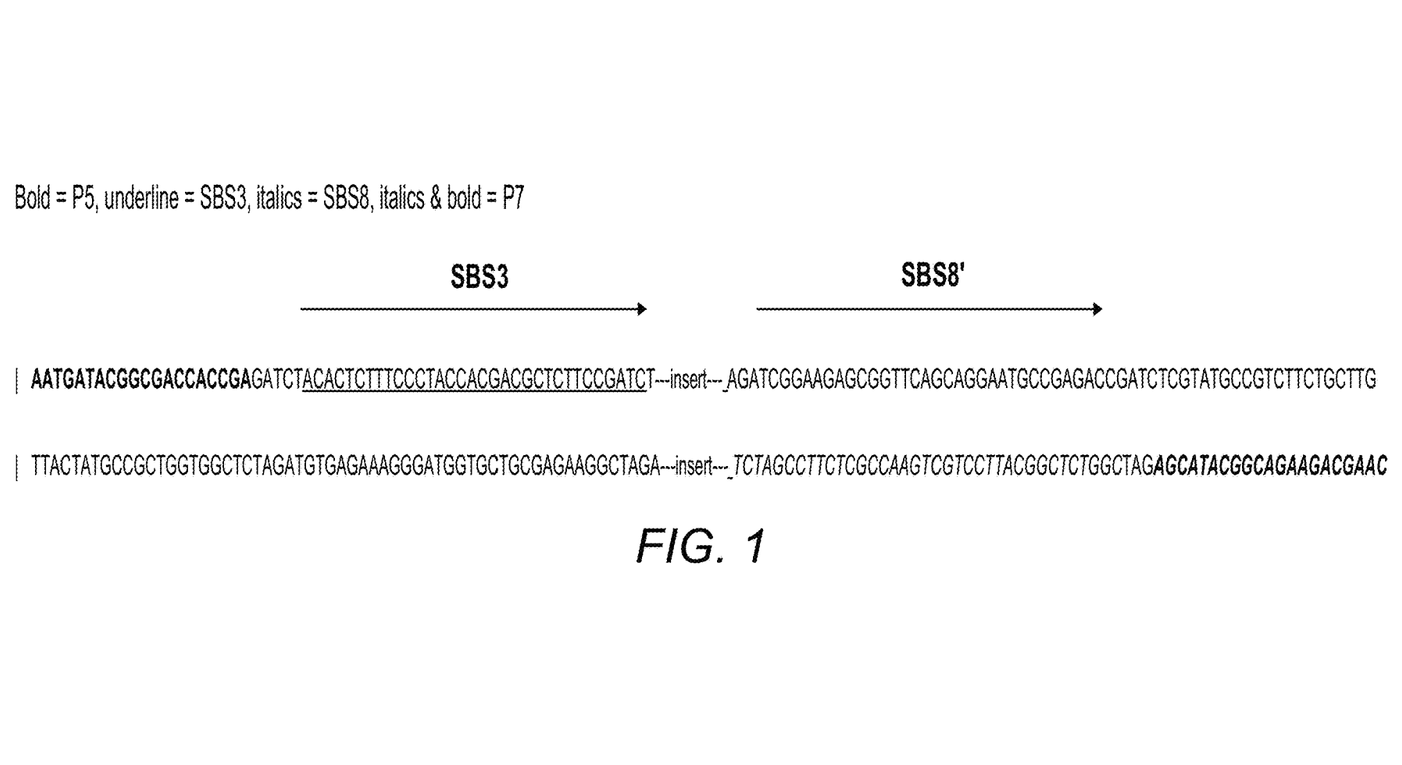

In order exemplify the invention a flowcell with v2 PhiX clusters was used. A standard construct comprising P5, SBS3, followed by a T residue then a genomic insert, SBS8' followed by an A residue and P7 as shown in FIG. 1 and below;

FIG. 1

SBS3/SBS8 std PE construct

```
Bold = P5, underline = SBS3, italics = SBS8,
italics & bold = P7
(SEQ ID NO: 03):
```

-continued
AATGATACGGCGACCACCGAGATCTACACTCTTTCCCTACCACGACGCTC

TTCCGATCT---insert---

(SEQ ID NO: 04):
TTACTATGCCGCTGGTGGCTCTAGATGTGAGAAAGGGATGGTGCTGCGAG

AAGGCTAGA---insert---

(SEQ ID NO: 05):
AGATCGGAAGAGCGGTTCAGCAGGAATGCCGAGACCGATCTCGTATGCCG

TCTTCTGCTTG (SEQ ID NO: 06):
TCTAGCCTTCTCGCCAAGTCGTCCTTACGGCTCTGGCTAG*AGCATACG*

*GCAGAAGACGAAC*

SBS3, SBS3+T and SBS8' primers were hybridised both alone and in combinations as shown in the table 1 below.

TABLE 1

| Lane | Primer hyb | Expected 1$^{st}$ cycle |
|---|---|---|
| 1 | SBS3 | T |
| 2 | SBS3 + T | All 4 (as genomic) |
| 3 | SBS8' | A |
| 4 | SBS3/SBS8' | T + A |
| 5 | SBS3 + T/SBS8' | All 4 (as genomic) + A |

Figure 2:
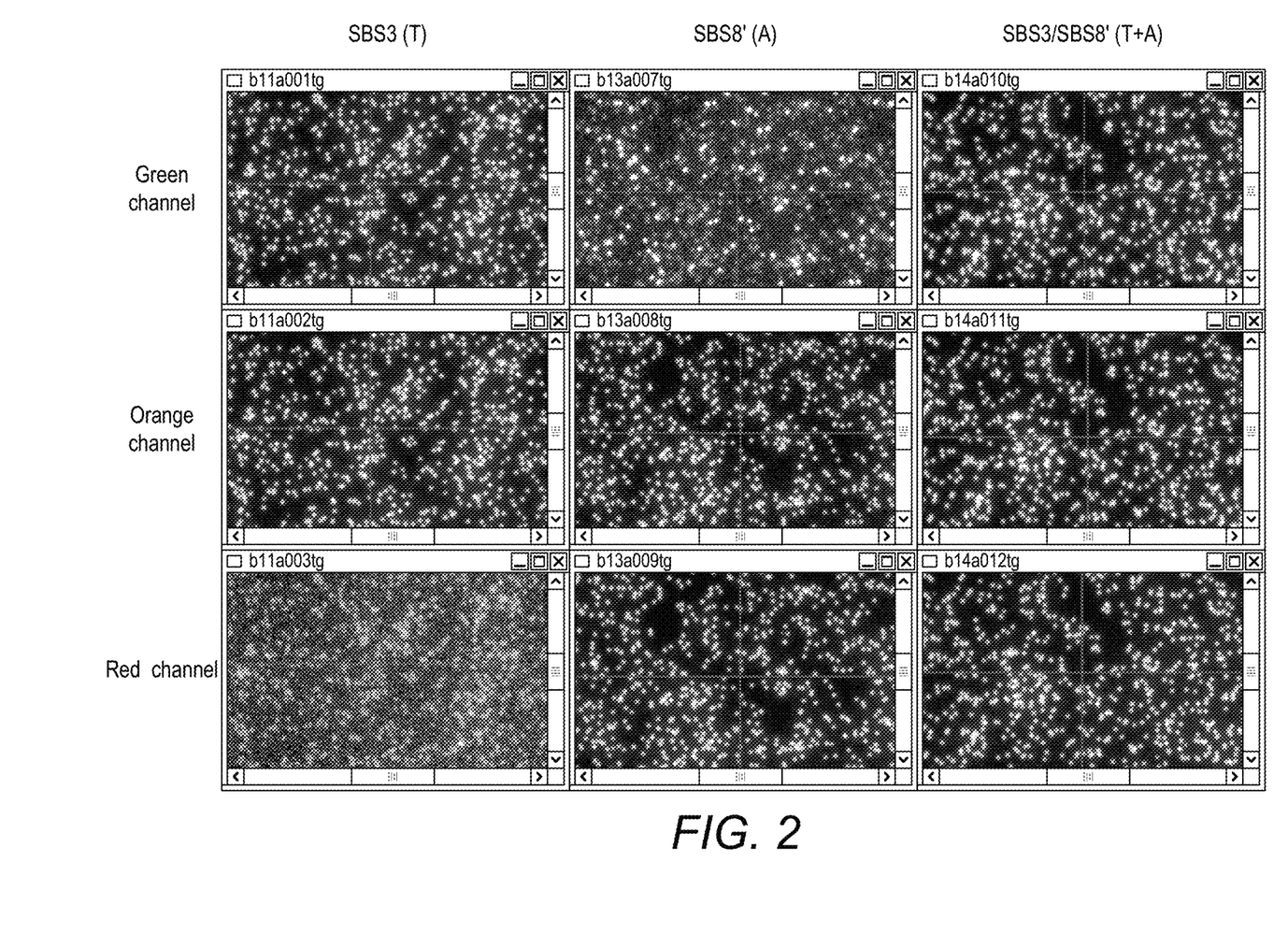

A first cycle of sequencing is carried out and the first images of the flowcell are obtained. FIG. 2 shows the 1$^{st}$ cycle individual scans in grayscale for the 3 channels looked at (green, orange and red). Lanes 1 and 3 have strongest signals in different 2 out of the 3 channels, while lane 4 has strong signals for all 3 channels due to the mixture of T and A bases being incorporated on SBS3 and SBS8' in that lane. T incorporation on SBS3 shows up as strong signal in green and orange channels, very weak in red. Incorporation of A on SBS8' shows up as strong in orange and red channels, mixture of weak and strong signal in green channel SBS3/SBS8' lane shows strong signal in green, orange and red channels due to incorporation of T and A on the 2 primers used.

Figure 3:
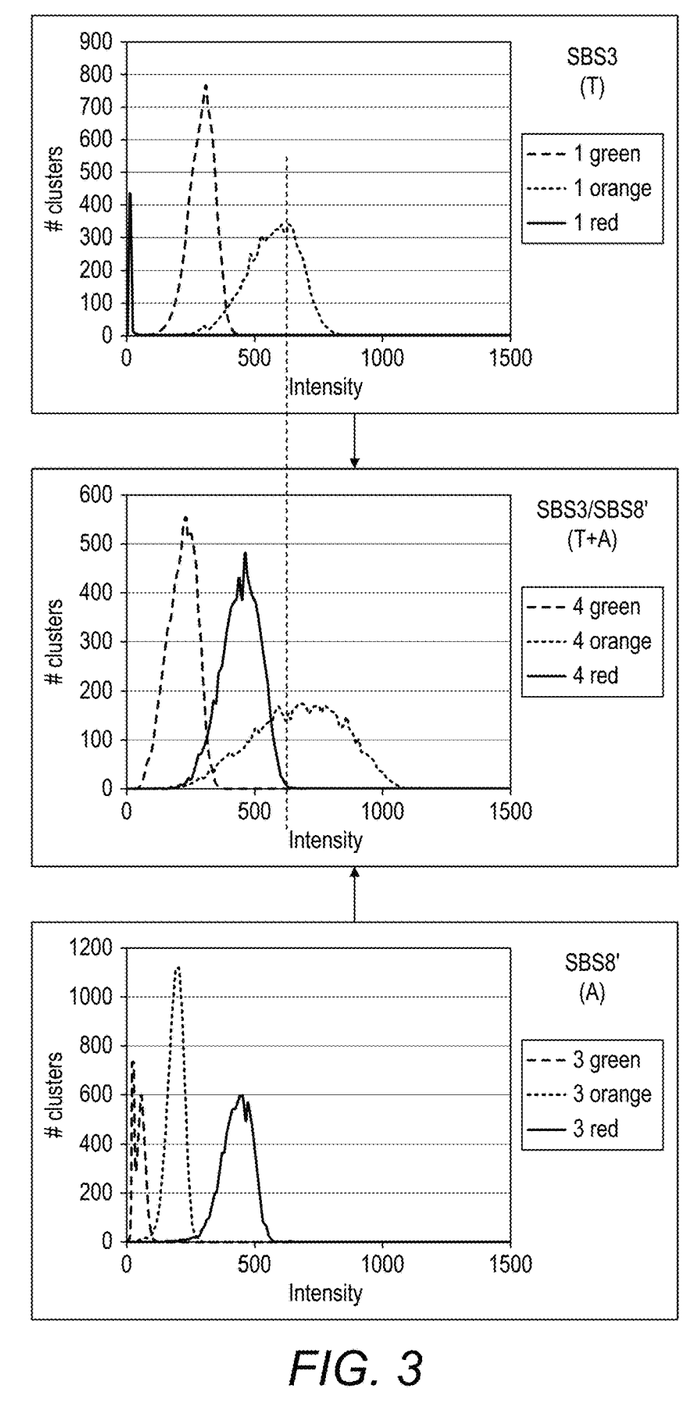

As can be seen in FIG. 3, intensity histograms show that the combined signals result in different intensity information being obtained which can then be allocated to base information to allow effective base calling. The upper histogram is from SBS3 alone, indicative of a T base call, the lower histogram is from SBS8' alone, indicative of an A base call whilst the central histogram shows the combined SBS3/SBS8' histogram where both an A base call and a T base call is being made, one from each of the extension reads.

Figure 4:
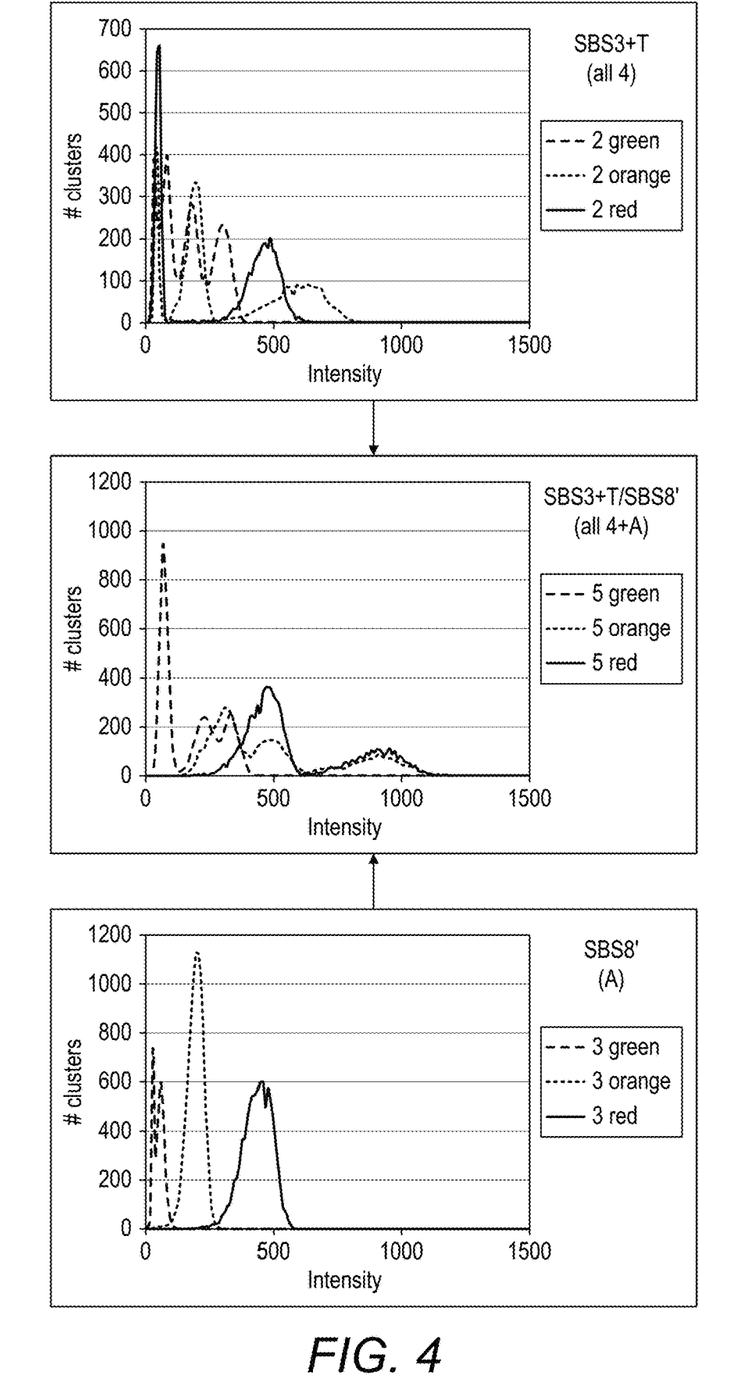

Similarly, FIG. 4 again shows intensity histograms, this time the upper histogram is from SBS3+T alone, where the base call can be any of the 4 bases as it related to genomic DNA, the lower histogram is from SBS8' alone, indicative of an A base call, whilst the central histogram shows the combined SBS3+T/SBS8' histogram where the base call can be any of the 4 bases as it related to genomic DNA from one extension read, plus a base call of A from the other extension read giving a double intensity peak from A/A clusters.

Once intensity readings and imaging has been obtained, base calls can be made for each location with multiple calls being made at each position for each cycle of sequencing. Each call at each position will then need to be allocated to the correct extension read. This can be done chemically, for example by making one of the reads brighter than the other by using a mixture of blocked and unblocked primer. Another option is to use bioinformatics information to determine which the more statistically "correct" base call is if we are using for example human inserts, or E. coli inserts etc.

In a particular embodiment, the multiple primers may be overlapping primers. For example SBS3 and SBS3+T could be used to sequence 2 consecutive bases at each cycle to give better accuracy by interrogating each base multiple times, in this case where two primers differing by a single base addition are used each base is interrogated twice.

In some cases blocked and unblocked primers are used to chemically differentiate between extension reads. For example, one of the primers would be completely unblocked at the start, whereas the other primer would be a mix of blocked/unblocked primers. So e.g. primer 1 would be 100% unblocked and give a 100% signal on sequencing. Then "primer 2" would be a mix of say 25% unblocked and 75% blocked, meaning that on sequencing you would get a 25% signal from this primer site. Therefore you would end up with the 2 reads giving data at 2 different levels (100% and 25%), which should make it easier to differentiate which base belongs to which read).

When bioinformatics information is used to allocate said bases to an extension read it is possible to bioinformatically search for the most likely reads possible from the mixture of bases being read e.g. if your reads are:

A/G, A/G, T/T, C/G, C/C, A/T

Then a search could be carried out in the genomes being sequenced for likely matches, and it may be possible to distinguish the 2 reads as being:

R1, human, AGTCCT

R2, E. coli, GATGCA as opposed to any other possible read from the mixture of bases above (e.g. AATCCA is not found in either genome). Longer reads would be more likely to be unique for each genome.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of nucleotides at the features of the array. An image can be obtained after the array is treated with a particular nucleotide type (e.g. A, T, C or G) Images obtained after addition of each nucleotide type will differ with regard to which features in the array are detected. These differences in the image reflect the different sequence content of the features on the array.

However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analysed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e g, minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Sequencing by ligation is a well known method for sequencing that requires repeated or prolonged irradiation of di-base probes with light. Exemplary systems that use sequencing by synthesis include the SOLiD™ system by Applied Biosystems (Life Technologies, Carlsbad, Calif.). Briefly, methods for sequencing by ligation include hybridizing sequencing primers to adapter sequences immobilized to templated beads. A set of four fluorescently labeled di-base probes compete for ligation to the sequencing primer. Specificity of the di-base probe is achieved by interrogating every 1st and 2nd base in each ligation reaction. Following a series of ligation cycles, the extension product is removed and the template is reset with a sequencing primer complementary to the n−1 position for a second round of ligation cycles. Multiple cycles of ligation, detection and cleavage are performed with the number of cycles determining the eventual read length.

In addition, the methods and solutions described herein can be particularly useful for sequencing from an array of nucleic acids, where multiple sequences can be read simultaneously from multiple positions on the array since each nucleotide at each position can be identified based on its identifiable label. Exemplary methods are described in US 2009/0088327; US 2010/0028885; and US 2009/0325172

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein. In certain embodiments a single pore may be used to hold the DNA strand, two which two or more primers are hybridised. Optical based sequencing by synthesis may then be performed.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties) Images obtained from such methods can be stored, processed and analyzed as set forth herein. In certain embodiments two polymerases may be present in the bottom of each well, each generating sequence data from a different primer attached to the same template molecule.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. More specifically, methods set forth herein can be used to produce clonal population of amplicons that are used to detect protons. In an embodiment using a pyrosequencing method, using two or more primers per strand of nucleic acid may mean more signal per unit time to deconvolve. In the pyrosequencing method, twice the normal drop in pH is flushed over may mean 1 of the primers had TT incorporation, or each primer had a single T incorporation.

The above methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

Nucleic Acid Amplification

In some embodiments, the immobilized DNA fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized.

In other embodiments, the immobilized DNA fragments are amplified in solution. For example, in some embodiments, the immobilized DNA fragments are cleaved or otherwise liberated from the solid support and amplification primers are then hybridized in solution to the liberated molecules. In other embodiments, amplification primers are hybridized to the immobilized DNA fragments for one or more initial amplification steps, followed by subsequent amplification steps in solution. Thus, in some embodiments an immobilized nucleic acid template can be used to produce solution-phase amplicons.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized DNA fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, Calif.) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'->3' exo- for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

What is claimed is:

1. A method for determining the sequence of a nucleic acid, comprising providing at least one nucleic acid bound to a support, wherein each nucleic acid has a nucleic acid strand;

hybridising at least two primers to the same strand of nucleic acid;

performing primer extensions on the same strand of nucleic acid at each of the at least two primers in the presence of labeled nucleotide bases to result in two primer extensions;

obtaining signal data corresponding to at least one labeled nucleotide base incorporated at each of the two primer extensions; and determining from said signal data the identity of the nucleotide bases and allocating said bases to an extension read to determine the sequence of the at least one nucleic acid.

2. The method of claim 1, wherein the method comprises contacting the at least one nucleic acid with an enzyme in the presence of (i) the at least two primers and (ii) four labelled nucleotide analogues selected from dGTP, dCTP, dTTP, dUTP, and dATP.

3. The method of claim 2, wherein each of the four labelled nucleotide analogues have a unique label which is different from the unique labels of the other three labelled nucleotide analogues.

4. The method of claim 2, wherein the method comprises the step of removing unbound labelled nucleotide analogues.

5. The method of claim 2, wherein the four labelled nucleotide analogues each comprises a single reversibly terminating nucleotide analogue or reversible terminator analogue.

6. The method of claim 2, wherein the unique label comprises a dye, a fluorophore, a chromophore, a combinatorial fluorescence energy transfer tag, a mass tag, or an electrophore.

7. The method of claim 2, wherein the enzyme comprises a polymerase or ligase.

8. The method of claim 2, wherein the same set of four labelled nucleotide analogues are used for each extension read.

9. The method of claim 1, wherein the at least two primers comprise blocked and unblocked primers to chemically differentiate between each extension read.

10. The method of claim 1, wherein the support comprises a chip or a bead.

11. The method of claim 1, wherein the least two primers have overlapping sequences.

12. The method of claim 1, wherein the at least two primers differ by a single base addition.

13. The method of claim 1, wherein bioinformatics information is used to allocate the bases to the extension read.

14. The method of claim 1, wherein the signal data corresponding to each of the at least two primer extensions is obtained substantially simultaneously.

15. The method of claim 1, wherein the step of determining the identity of the nucleotide bases comprises analysing a signal intensity profile corresponding to unique labels detected at each of the plurality of extension reads.

16. The method of claim 1, wherein the signal data comprises one or more images.

17. The method of claim 16, wherein the signal data is detected as colour signals corresponding to a plurality of nucleotide analogues incorporating the primer extensions and wherein each colour signal corresponds to a different nucleotide analogue or combination of nucleotide analogues.

18. The method of claim 1, wherein the method comprises the step of signal processing comprising one or more of signal deconvolution, signal refinement and signal selection.

19. The method of claim 1, wherein multiple base calls are made at each hybridisation cycle.

20. The method of claim 1, wherein the step of allocating the bases to an extension read comprises determining the position of the nucleotide bases.

21. The method of claim 1, wherein the step of allocating the bases to an extension read comprises providing a preliminary base call and a final base call for each extension read.

22. The method of claim 21, wherein the final base call is provided by comparison of the preliminary base call data with a reference genome.

23. A method for determining the sequence of a nucleic acid, comprising
providing at least one nucleic acid bound to a support, wherein each nucleic acid has a nucleic acid strand;
hybridising at least two primers to the same strand of nucleic acid;
performing primer extensions on the same strand of nucleic acid at each of the at least two primers in the presence of labeled nucleotide bases to result in two primer extensions;
obtaining signal data corresponding to at least one labeled nucleotide base incorporated at each of the two primer extensions; and
determining from said signal data the identity of the nucleotide bases and allocating said bases to an extension read to determine the sequence of the at least one nucleic acid, wherein the at least two primers comprise blocked and unblocked primers to differentiate between each extension read.

24. The method of claim 23, wherein the at least two primers comprises a first unblocked primer having a first nucleotide sequence and a second mixture of unblocked and blocked primers having a second nucleotide sequence.

25. The method of claim 24, wherein determining the identity of the nucleotides bases comprises determining the signal intensity of newly added labeled nucleotide bases from the first unblocked primer and the second mixture of blocked and unblocked primers.

* * * * *